US00PP17847P2

(12) United States Plant Patent
Smith

(10) Patent No.: US PP17,847 P2
(45) Date of Patent: Jul. 3, 2007

(54) ***CHRYSANTHEMUM* PLANT NAMED 'BRIGHT YOGRETCHEN'**

(50) Latin Name: *Chrysanthememum×morifolium*
Varietal Denomination: Bright Yogretchen

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 27 days.

(21) Appl. No.: 11/269,187

(22) Filed: Nov. 8, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Chrysanthemum* plant named 'Bright Yogretchen', characterized by its compact, upright and mounded plant habit; freely branching habit; dense and full plants; uniform and freely flowering habit; medium-sized decorative-type inflorescences with elongated oblong-shaped ray florets; golden yellow-colored ray florets; and natural season flowering in mid-September in the Northern Hemisphere.

2 Drawing Sheets

Botanical designation: *Chrysanthemum×morifolium.*
Cultivar denomination: 'Bright Yogretchen'.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Bright Yogretchen'.

The new cultivar is a product of a planned breeding program conducted by the Inventor in Alva, Fla. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Sunny Yogretchen, disclosed in U.S. Plant Pat. No. 15,511. The new *Chrysanthemum* was discovered and selected by the Inventor as a single flowering plant from within a population of plants of the cultivar Sunny Yogretchen in a controlled environment in Alva, Fla. in April, 2003. The selection of this plant was based on its desirable inflorescence form, attractive ray floret color and good garden performance.

Asexual reproduction of the new cultivar by terminal vegetative cuttings in a controlled environment in Alva, Fla. since June, 2003, has shown that the unique features of this new *Chrysanthemum* are stable and reproduced true to type in successive generations.

SUMMARY OF THE INVENTION

The cultivar Bright Yogretchen has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bright Yogretchen'. These characteristics in combination distinguish 'Bright Yogretchen' as a new and distinct cultivar:

1. Compact, upright and mounded plant habit.
2. Freely branching habit; dense and full plants.
3. Uniform and freely flowering habit.
4. Medium-sized decorative-type inflorescences with elongated oblong-shaped ray florets.
5. Golden yellow-colored ray florets.
6. Natural season flowering in mid-September in the Northern Hemisphere.

In side-by-side comparisons conducted in Alva, Fla., plants of the new *Chrysanthemum* differed from plants of the parent, the cultivar Sunny Yogretchen, primarily in ray floret coloration as plants of the cultivar Sunny Yogretchen had yellow bronze-colored ray florets. In addition, plants of the new *Chrysanthemum* were shorter and flowered about two to three days later than plants of the cultivar Sunny Yogretchen when grown under natural season conditions.

Plants of the new *Chrysanthemum* can be compared to plants of the *Chrysanthemum* cultivar Sunny Yomarilyn, disclosed in U.S. Plant Pat. No. 13,846. In side-by-side comparisons conducted in Alva, Fla., plants of the new *Chrysanthemum* differed from plants of the cultivar Sunny Yomarilyn in the following characteristics:

1. Plants of the new *Chrysanthemum* were stronger than plants of the cultivar Sunny Yomarilyn.
2. Plants of the new *Chrysanthemum* were not as broad as plants of the cultivar Sunny Yomarilyn.
3. Plants of the new *Chrysanthemum* had smaller inflorescences than plants of the cultivar Sunny Yomarilyn.
4. Ray florets of plants of the new *Chrysanthemum* were richer yellow in color than ray florets of plants of the cultivar Sunny Yomarilyn.

Plants of the new *Chrysanthemum* can also be compared to plants of the *Chrysanthemum* cultivar Gedi One Cen, disclosed in U.S. Plant Pat. No. 13,902. In side-by-side comparisons conducted in Alva, Fla., plants of the new *Chrysanthemum* differed from plants of the cultivar Gedi One Cen in the following characteristics:

1. Plants of the new *Chrysanthemum* were larger than plants of the cultivar Gedi One Cen.
2. Ray florets of plants of the new *Chrysanthemum* were more yellow in color than ray florets of plants of the cultivar Gedi One Cen.
3. Plants of the new *Chrysanthemum* had fewer disc florets per inflorescence than plants of the cultivar Gedi One Cen.
4. Ray floret color of plants of the new *Chrysanthemum* was longer lasting than ray floret color of plants of the cultivar Gedi One Cen.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Bright Yogretchen' grown in a container.

The photograph on the second sheet comprises a close-up view of typical inflorescences of the 'Bright Yogretchen'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the summer in a glass-covered greenhouse and under conditions and practices which approximate those generally used in commercial garden-type *Chrysanthemum* production. Rooted cuttings were planted in 15.25-cm containers, grown under artificial long day conditions (four-hour night interruption) and pinched about ten days later. About ten days after the pinch, plants were then exposed to artificial short day conditions (11.5 hours light) until flowering. During the production of the plants, temperatures ranged from 18° C. to 38° C. Measurements and numerical values represent averages for typical flowering plants.

Botanical classification: *Chrysanthemum×morifolium* cultivar Bright Yogretchen.

Commercial classification: Decorative-type garden *Chrysanthemum*.

Parentage: Naturally-occurring whole plant mutation of the *Chrysanthemum×morifolium* cultivar Sunny Yogretchen, disclosed in U.S. Plant Pat. No. 15,511.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown. Stems initially upright, then somewhat outwardly spreading; compact and mounded growth habit. Freely branching with lateral branches potentially forming at every node. Moderately vigorous.

*Plant height.*—About 21 cm.

*Plant diameter.*—About 38 cm.

*Lateral branches.*—Length: About 19 cm. Diameter: About 5 mm. Internode length: About 1.5 cm. Aspect: Upright and outwardly spreading. Texture: Pubescent. Color: 144A to 146A.

*Foliage description.*—Leaf arrangement: Alternate. Length: About 2.4 cm. Width: About 1.5 cm. Apex: Mucronate. Base: Attenuate. Margin: Palmately lobed, sinuses divergent. Texture, upper surface: Slightly pubescent. Texture, lower surface: Pubescent; veins prominent. Color: Developing and fully expanded foliage, upper surface: More green than 147A. Developing and fully expanded foliage, lower surface: More green than 147B. Venation, upper surface: More green than 147A. Venation, lower surface: Close to 147B. Petiole length: About 7.5 mm. Petiole diameter: About 3 mm. Petiole color, upper and lower surfaces: Close to 146B.

Inflorescence description:

*Appearance.*—Decorative-type inflorescence form with elongated oblong-shaped ray florets. Inflorescences borne on terminals above foliage, arising from leaf axils. Ray florets developing acropetally on a capitulum. About eight inflorescences per lateral branch.

*Flowering response.*—Under natural season conditions, plants flower in mid-September in the Northern Hemisphere.

*Inflorescence bud (before showing color).*—Height: About 6 mm. Diameter: About 6 mm. Shape: Spherical. Color: (lower surface of phyllaries): Darker green than 147A.

*Inflorescence size.*—Diameter: About 3.5 cm. Depth (height): About 1.2 cm. Disc diameter: About 3.5 mm; inconspicious. Receptacle diameter: About 4 mm.

*Ray florets.*—Shape: Elongated oblong-shaped. Length: About 1.7 cm. Width: About 6 mm. Corolla tube length: About 3 mm. Corolla tube diameter: About 1 mm. Apex: Emarginate, acute or rounded. Margin: Fused. Texture, upper and lower surfaces: Smooth, glabrous; satiny. Orientation: Initially upright, then perpendicular to the peduncle. Number of ray florets per inflorescence: About 110 in numerous whorls. Color: When opening, upper and lower surfaces: Close to 9A. Fully opened, upper surface: Close to 12A. Fully opened, lower surface: Close to 9A.

*Disc florets.*—Shape: Tubular, elongated. Length: About 2 mm. Width, apex: About 1 mm. Width, base: About 1 mm. Number of disc florets per inflorescence: About twelve. Color: Immature: Close to 144A. Mature: Apex: Close to 9A. Mid-section: 144C. Base: Close to 155D.

*Phyllaries.*—Quantity per inflorescence: About eight. Length: About 5 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 144A. Color, lower surface: Darker green than 147A.

*Peduncle.*—Length: First peduncle: About 3.4 cm. Fourth peduncle: About 4.3 cm. Diameter: About 2 mm. Strength: Strong. Aspect: About 40° from vertical. Texture: Pubescent. Color: Close to 144A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 4 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° C. to more than 38° C.

It is claimed:

1. A new and distinct cultivar of *Chrysanthemum* plant named 'Bright Yogretchen', as illustrated and described.

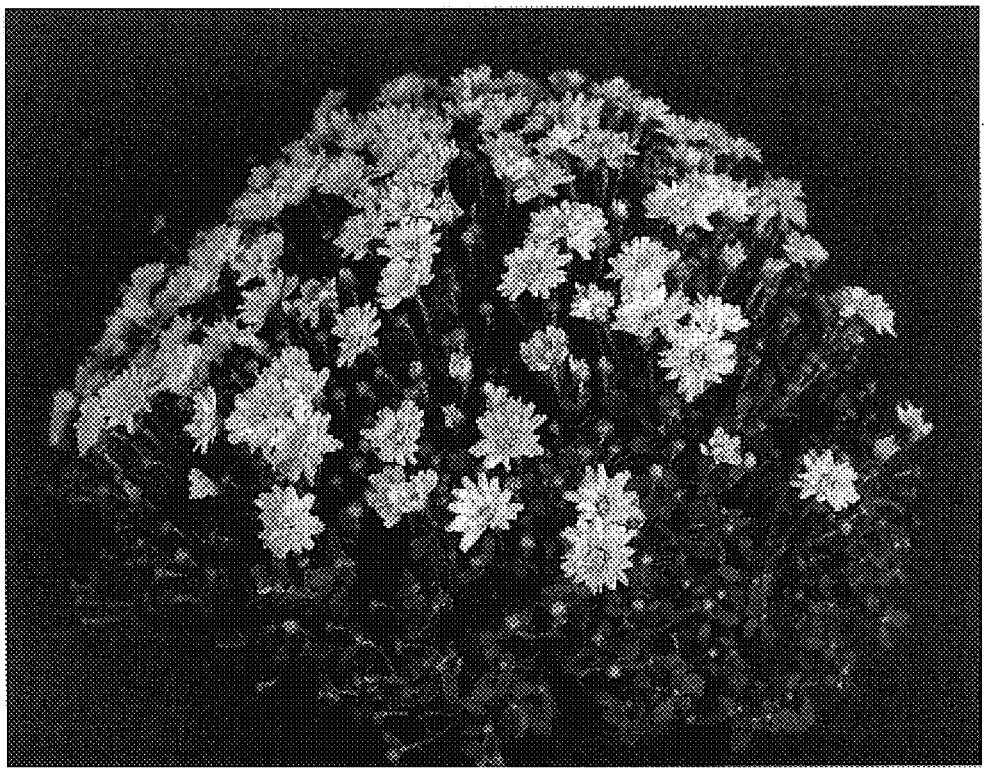

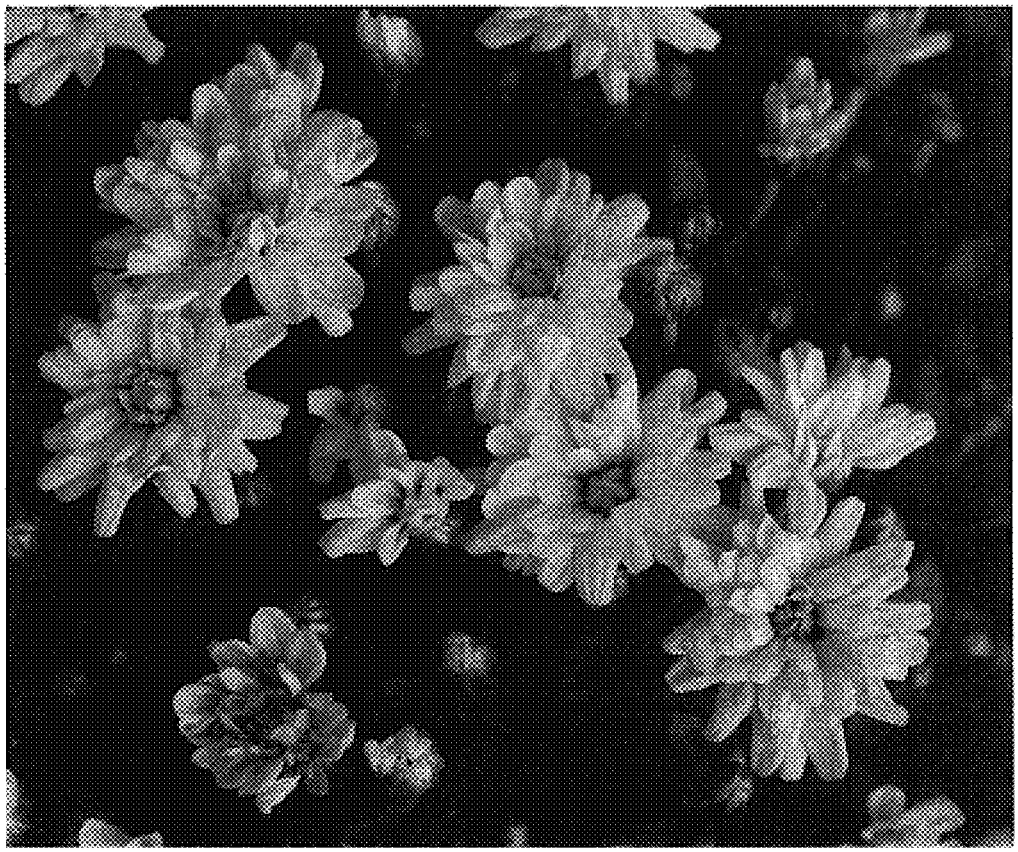

* * * * *